United States Patent
Jacks et al.

(10) Patent No.: US 10,845,330 B2
(45) Date of Patent: *Nov. 24, 2020

(54) PHYSIOLOGICAL CHARACTERISTIC SENSORS AND METHODS FOR FORMING SUCH SENSORS

(71) Applicant: MEDTRONIC MINIMED, INC., Northridge, CA (US)

(72) Inventors: Steven C. Jacks, Los Angeles, CA (US); Raghavendhar Gautham, Los Angeles, CA (US); Bradley C. Liang, Bloomfield Hills, MI (US); Megan E. Little, Claremont, CA (US); Daniel E. Pesantez, Canoga Park, CA (US); Rajiv Shah, Rancho Palos Verdes, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 633 days.

This patent is subject to a terminal disclaimer.

(21) Appl. No.: 15/595,687

(22) Filed: May 15, 2017

(65) Prior Publication Data

US 2017/0248542 A1     Aug. 31, 2017

Related U.S. Application Data

(63) Continuation of application No. 14/267,739, filed on May 1, 2014, now Pat. No. 9,681,828.

(51) Int. Cl.
*C25D 3/52* (2006.01)
*C25D 5/18* (2006.01)
(Continued)

(52) U.S. Cl.
CPC ......... *G01N 27/416* (2013.01); *A61B 5/1451* (2013.01); *A61B 5/14532* (2013.01);
(Continued)

(58) Field of Classification Search
CPC ... C25D 5/18; C25D 3/50; C25D 3/52; C25D 3/567
See application file for complete search history.

(56) References Cited

U.S. PATENT DOCUMENTS 4,755,173 A    7/1988 Konopka et al.
5,391,250 A    2/1995 Cheney, II et al.
(Continued)

OTHER PUBLICATIONS

Chandrasekar et al., "Pulse and Pulse Reverse Plating—Conceptual, Advantages and Applications" Electrochim. Acta 53, pp. 3313-3322 (2008). (Year: 2008).*

*Primary Examiner* — Brian W Cohen
(74) *Attorney, Agent, or Firm* — Lorenz & Kopf, LLP

(57) ABSTRACT

A physiological characteristic sensor, a method for forming a physiological characteristic sensor, and a method for forming a platinum deposit having a rough surface are presented here. The method for forming a physiological characteristic sensor includes immersing a sensor electrode in a platinum electrolytic bath. Further, the method includes performing an electrodeposition process by sequentially applying a pulsed signal to the sensor electrode, wherein the pulsed signal includes a repeated cycle of a first current and a second current different from the first current, and applying a non-pulsed continuous signal to the sensor electrode, wherein the non-pulsed continuous signal includes a non-repeated application of a third current, to form a platinum deposit on the sensor electrode.

20 Claims, 7 Drawing Sheets

(51) Int. Cl.
  *C25D 3/56* (2006.01)
  *G01N 27/416* (2006.01)
  *G01N 27/327* (2006.01)
  *C23C 28/00* (2006.01)
  *A61B 5/145* (2006.01)
  *C25D 7/00* (2006.01)
  *G01N 27/30* (2006.01)

(52) U.S. Cl.
  CPC ............... *C23C 28/00* (2013.01); *C25D 3/52* (2013.01); *C25D 3/567* (2013.01); *C25D 5/18* (2013.01); *C25D 7/00* (2013.01); *G01N 27/327* (2013.01); *A61B 2562/02* (2013.01); *A61B 2562/125* (2013.01); *G01N 27/30* (2013.01)

(56) References Cited

U.S. PATENT DOCUMENTS

| | | |
|---|---|---|
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,080,504 A | 6/2000 | Taylor et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,306,277 B1 | 10/2001 | Strangman et al. |
| 6,340,421 B1 | 1/2002 | Vachon et al. |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,887,681 B2 | 2/2011 | Zhou |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 9,681,828 B2 * | 6/2017 | Jacks .................. A61B 5/14532 |
| 2003/0102226 A1 | 6/2003 | Gabe et al. |
| 2005/0016858 A1 | 1/2005 | Barstad et al. |
| 2007/0123819 A1 | 5/2007 | Mernoe et al. |
| 2007/0173711 A1 | 7/2007 | Shah et al. |
| 2010/0096278 A1 * | 4/2010 | Shah .................. G01N 27/307 205/777.5 |
| 2010/0160861 A1 | 6/2010 | Causey, III et al. |
| 2011/0152654 A1 | 6/2011 | Wang et al. |
| 2014/0243634 A1 | 8/2014 | Huang et al. |

\* cited by examiner

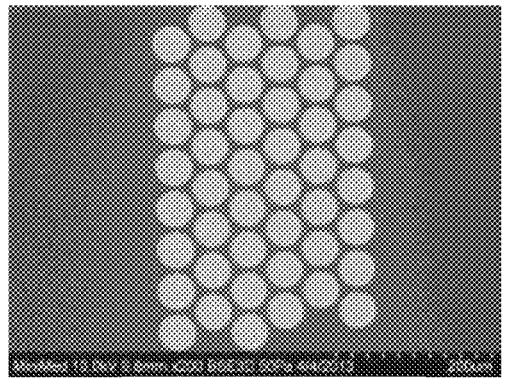
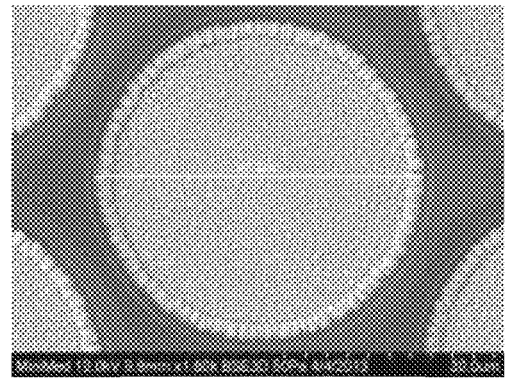
PRIOR ART
FIG. 9
PRIOR ART
FIG. 10
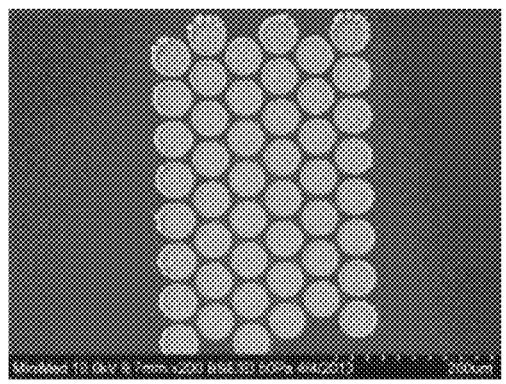
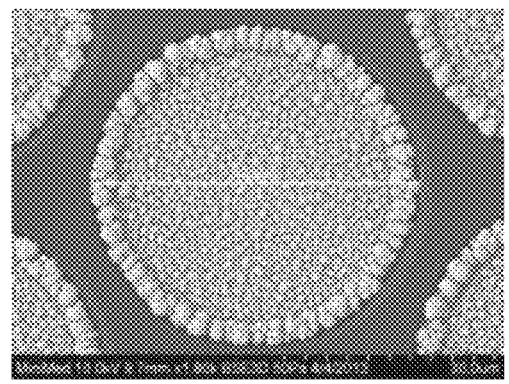
PRIOR ART
FIG. 11
PRIOR ART
FIG. 12
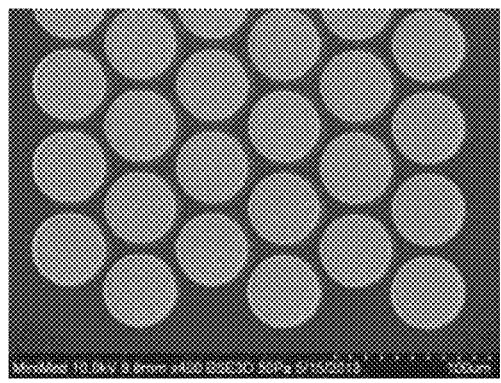
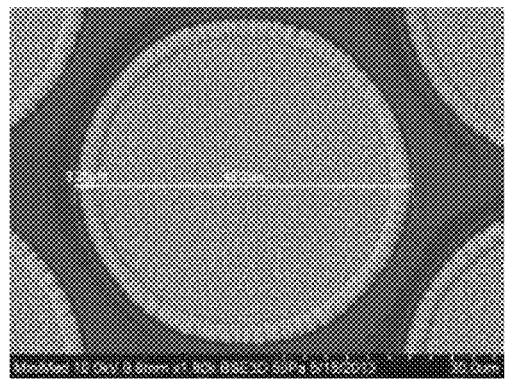
FIG. 13
FIG. 14

PHYSIOLOGICAL CHARACTERISTIC SENSORS AND METHODS FOR FORMING SUCH SENSORS

CROSS-REFERENCE TO RELATED APPLICATION

This application claims priority to U.S. patent application Ser. No. 14/267,739, filed May 1, 2014, which is incorporated herein by reference in its entirety.

TECHNICAL FIELD

Embodiments of the subject matter described herein relate generally to sensors for sensing and/or determining physiological characteristics of subcutaneous interstitial fluid, and more particularly, to such sensors that determine constituents of subcutaneous interstitial fluid, such as glucose levels in subcutaneous interstitial fluid, during in vivo or in vitro applications and to methods for forming such sensors.

BACKGROUND

The determination of glucose levels in subcutaneous interstitial fluid is useful in a variety of applications. One particular application is for use by diabetics in combination with an insulin infusion pump system. The use of insulin pumps is frequently indicated for patients, particularly for diabetics whose conditions are best treated or stabilized by the use of insulin infusion pumps. Glucose sensors are useful in combination with such pumps, since these sensors may be used to determine glucose levels and provide information useful to the system to monitor the administration of insulin in response to actual and/or anticipated changes in blood glucose levels. For example, glucose levels are known to change in response to food and beverage intake, as well as to normal metabolic function. While certain diabetics are able to maintain proper glucose-insulin levels with conventional insulin injection or other insulin administration techniques, some individuals experience unusual problems giving rise to the need for a substantially constant glucose monitoring system to maintain an appropriate glucose-insulin balance in their bodies.

Glucose, as a compound, is difficult to determine on a direct basis electrochemically, since its properties lead to relatively poor behavior during oxidation and/or reduction activity. Furthermore, glucose levels in subcutaneous interstitial fluid are difficult to determine inasmuch as most mechanisms for sensing and/or determining glucose levels are affected by the presence of other constituents or compounds normally found in subcutaneous interstitial fluid. For these reasons, it has been found desirable to utilize various enzymes and/or other protein materials that provide specific reactions with glucose and yield readings and/or by-products which are capable of analyses quantitatively.

For example, sensors have been outfitted with enzymes or other reagent proteins that are covalently attached to the surface of a working electrode to conduct electrochemical determinations either amperometrically or potentiometrically. When glucose and oxygen in subcutaneous interstitial fluid come into contact with the enzyme or reagent protein in the sensor, the glucose and oxygen are converted into hydrogen peroxide and gluconic acid. The hydrogen peroxide then contacts the working electrode. A voltage is applied to the working electrode, causing the hydrogen peroxide to breakdown into hydrogen, oxygen and two electrons. Generally, when glucose levels are high, more hydrogen peroxide is generated, and more electric current is generated and measured by the sensor. For such sensors, performance of the working electrode is directly correlated to the amount of conductive material forming the working electrode. Further, performance of the working electrode is inversely correlated to the impedance of the working electrode. Working electrodes having large surface areas and low impedance allow for a larger degree of hydrogen peroxide oxidation at the electrode surface, thereby generating a higher current and signal. However, there is a space constraint for working electrodes on sensors, particularly when utilizing multiple working electrodes across a sensor layout.

While amperometric sensors are commonly used to monitor glucose, embodiments of these sensors may encounter technical challenges when scaled. Specifically, smaller electrodes with reduced surface areas may have difficulty in effectively measuring glucose levels. In view of these and other issues, glucose sensors and methods for forming glucose sensors designed to enhance glucose sensing performance are desirable.

BRIEF SUMMARY

An exemplary embodiment of a method for forming a physiological characteristic sensor is provided. The exemplary method for forming a physiological characteristic sensor includes immersing a sensor electrode in a platinum electrolytic bath. Further, the method includes performing an electrodeposition process by sequentially applying a pulsed signal to the sensor electrode, wherein the pulsed signal includes a repeated cycle of a first current and a second current different from the first current, and applying a non-pulsed continuous signal to the sensor electrode, wherein the non-pulsed continuous signal includes a non-repeated application of a third current, to form a platinum deposit on the sensor electrode.

A method for forming a platinum deposit having a rough surface is provided herein. The method includes contacting a deposition site with a platinum electrolyte. The method further includes performing a hybrid pulse/continuous electrodeposition process by sequentially applying a pulsed signal to the deposition site and applying a non-pulsed continuous signal to the deposition site to form the platinum deposit on the deposition site. The pulsed signal includes a repeated cycle of a first current and a second current different from the first current. The non-pulsed continuous signal includes a non-repeated application of a third current.

Also provided is an exemplary embodiment of a method for forming a physiological characteristic sensor having a sensor base, an electrode located on the sensor base, a semipermeable membrane selective to an analyte positioned over the electrode, a reagent encapsulated between the semipermeable membrane and the electrode, a protein layer encapsulated between the semipermeable membrane and the electrode, and an adhesion promoter layer between the protein layer and the semipermeable membrane. The method includes performing an electrodeposition process to form a platinum coating as the sensor electrode, wherein the platinum coating has a cross sectional area and an electrochemical real surface area at least about 80 times greater than the cross sectional area.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIGS. 9-12 and 13-14 are scanning electron microscope/focused ion beam photographs of platinum deposit obtained from a prior art continuous current electrodeposition processes, and from a hybrid pulse/continuous electrodeposition process in accordance with the embodiments herein, respectively.

DETAILED DESCRIPTION

Figure 1:
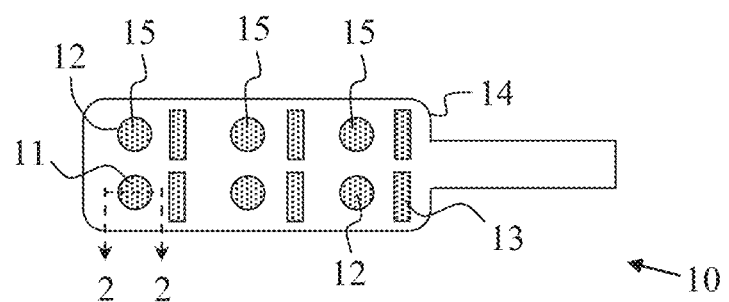
FIG. 1 is an overhead view of an exemplary embodiment of a physiological characteristic sensor during an exemplary formation process.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description. Also, while the preceding background discusses glucose sensing and exemplary physiological characteristic sensors are described as glucose sensors herein, such description is for convenience and is not limiting. The claimed subject matter may include any type of physiological characteristic sensor utilizing an embodiment of the sensor electrode described herein.

Embodiments of physiological characteristic sensors provided herein use biological elements to convert a chemical analyte in a matrix into a detectable signal. In certain embodiments, a physiological characteristic sensor of the type presented here is designed and configured for subcutaneous operation in the body of a patient. The physiological characteristic sensor includes electrodes that are electrically coupled to a suitably configured electronics module that applies the necessary excitation voltages and monitors the corresponding electrical responses (e.g., electrical current, impedance, or the like) that are indicative of physiological characteristics of the body of the patient. For the embodiment described here, the physiological characteristic sensor includes at least one working electrode, which is fabricated in a particular manner to provide the desired electrochemical characteristics. In this regard, for sensing glucose levels in a patient, the physiological characteristic sensor works according to the following chemical reactions:

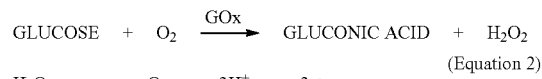

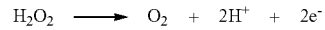

The glucose oxidase (GOx) is provided in the sensor and is encapsulated by a semipermeable membrane adjacent the working electrode. The semipermeable membrane allows for selective transport of glucose and oxygen to provide contact with the glucose oxidase. The glucose oxidase catalyzes the reaction between glucose and oxygen to yield gluconic acid and hydrogen peroxide (Equation 1). The $H_2O_2$ then contacts the working electrode and reacts electrochemically as shown in Equation 2 under electrocatalysis by the working electrode. The resulting current can be measured by a potentiostat. These reactions, which occur in a variety of oxidoreductases known in the art, are used in a number of sensor designs. As the size of glucose sensors and their components scale, the capability of the working electrode to efficiently electrocatalyze hydrogen peroxide is reduced. Embodiments of physiological characteristic sensors and methods for forming physiological characteristic sensors are provided herein to enhance sensor electrode performance despite scaling.

Figure 2:
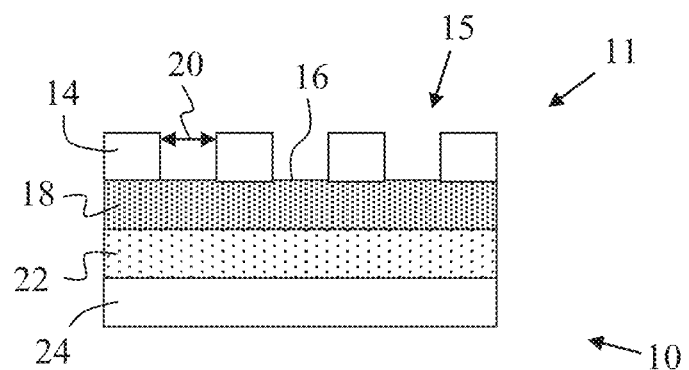
FIG. 2 is a cross-sectional view taken along line 2-2 in FIG. 1 of the exemplary embodiment of a physiological characteristic sensor during formation.

FIG. 1 is a schematic representation of an exemplary embodiment of a partially formed physiological characteristic sensor 10. FIG. 2 is a cross-sectional view of the partially formed physiological characteristic sensor 10 of FIG. 1. The sensor 10 is suitably configured to measure a physiological characteristic of the subject, e.g., a human patient. In accordance with the non-limiting embodiments presented here, the physiological characteristic of interest is blood glucose, and the sensor 10 generates output that is indicative of a blood glucose level of the subject. It should be appreciated that the techniques and methodologies described here may also be utilized with other sensor types if so desired.

The sensor 10 includes sensor electrodes 11 designed for subcutaneous placement at a selected site in the body of a user. When placed in this manner, the sensor electrodes 11 are exposed to the user's bodily fluids such that they can react in a detectable manner to the physiological characteristic of interest, e.g., blood glucose level. In certain embodiments, the sensor electrodes 11 may include one or more working electrodes 12, adjacent counter electrodes 13, and reference electrodes (not shown). For the embodiments described here, the sensor electrodes 11 employ thin film electrochemical sensor technology of the type used for monitoring blood glucose levels in the body. Further description of flexible thin film sensors of this general type are found in U.S. Pat. No. 5,391,250, entitled METHOD OF FABRICATING THIN FILM SENSORS, which is herein incorporated by reference. In other embodiments, different types of implantable sensor technology, such as chemical based, optical based, or the like, may be used.

The sensor electrodes 11 cooperate with sensor electronics, which may be integrated with the sensor electrodes 11 in a sensor device package, or which may be implemented in a physically distinct device or component that communicates with the sensor electrodes 11 (such as a monitor device, an infusion pump device, a controller device, or the like). In this regard, any or all of the remaining elements shown in FIG. 1 may be included in the sensor electronics, as needed to support the particular embodiment.

In the embodiment of FIG. 1, two working electrodes 12 are provided and are formed as two rows of three subsections 15. While the subsections 15 are shown as having the shape of circles, the working electrodes 12 may be formed having the shape of squares, rectangles, or other shapes as desired. While the exemplary physiological characteristic sensor 10 of FIG. 1 includes two working electrodes 12, it is envisioned that the physiological characteristic sensor 10 may include any practical number of working electrodes 12, such as one, four, six, eight, or fewer or more as desired.

In FIG. 1, each circular subsection 15 of the working electrodes 12 is formed with a surface of micro-circles having diameters of about 40 μm or about 48 μm. Other sizes may be suitable, for example, an embodiment with four working electrodes 12 may utilize circular subsections 15 formed with micro-circle having diameters of about 52 μm. As illustrated, subsections of the exemplary counter electrodes 13 are formed adjacent each circular subsection 15 of the working electrodes 12. The subsections of the counter electrodes 13 are rectangular shaped, though other shapes may be utilized as desired.

The micro-circles and circular subsections 15 of the working electrodes 12 and the counter electrodes 13 defining the sensor electrodes 11 of FIG. 1 are surrounded by an electrical insulation layer 14. An exemplary insulation layer 14 is polyimide. An exemplary insulation layer has a thickness of from about 4 μm to about 10 μm, such as about 7 μm.

In FIG. 2, it can be seen that the micro-circles of the subsections 15 of the sensor electrode 11 are formed by the surfaces 16 of a metallization layer 18 that are exposed by holes, gaps, or voids formed in the overlying insulation layer 14. The exposed surfaces 16 may have a diameter, indicated by double-headed arrow 20, of from about 10 μm to about 100 μm, such as about 40 μm. An exemplary metallization layer 18 is a gold material, though other suitable conductive metals may be used. The exemplary metallization layer 18 has a thickness of from about 4000 Angstroms to about 7000 Angstroms, such as about 5000 Angstroms. As shown, the exemplary metallization layer 18 is formed on an adhesion layer 22. Depending on the composition of the metallization layer 18, an adhesion layer 22 may not be needed. Specifically, certain metals do not need an adhesion layer to assist in adhesion. In an exemplary embodiment, adhesion layer 22 is a chromium-based material, though other materials suitable for assisting adhesion of the metallization layer 18 may be used. As shown, the physiological characteristic sensor 10 further includes a base layer 24. The base layer 24 may be any suitable insulator, such as, for example, polyimide. An exemplary base layer 24 has a thickness of from about 8 μm to about 18 μm, such as about 12 μm.

In an exemplary embodiment, the physiological characteristic sensor 10 is formed by sputtering the adhesion layer 22 onto the base layer 24. Then, the metallization layer 18 is sputtered onto the adhesion layer. Thereafter, the insulation layer 14 is formed on the metallization layer 18. The insulation layer 14 may be patterned after application onto the metallization layer 18 to expose the surfaces 16 of the metallization layer 18 forming the sensor electrodes 11.

After formation of the physiological characteristic sensor 10 shown in FIGS. 1 and 2, the exemplary method forms a platinum electrode deposit over the exposed surfaces 16 of the metallization layer 18. The exemplary method uses a hybrid pulse/continuous signal electrodeposition process to form the platinum electrode deposit with a rough surface, thereby increasing the surface area of the platinum electrode deposit without requiring an increase in the cross sectional area of the platinum electrode deposit. As used herein, the "cross sectional area" of the platinum electrode deposition is substantially equal to the exposed surface area of the surfaces 16 of the metallization layer 18. The ratio of deposited platinum in $cm^2$ (or real surface area) to the geometric surface area of exposed metallization layer 18 in $cm^2$ on the sensor electrode is the surface area ratio (SAR). The real surface area may be determined, and the SAR may be calculated, using cyclic voltammetry. The SAR will vary depending on the type of electrode layout and the platinum deposition method used. Exemplary embodiments have an electrode platinum SAR in the range of about 200 to about 400 on the sensor electrode. Certain embodiments may have an electrode platinum SAR of greater than about 80, such as greater than about 100 if the number of pulse cycles and/or continuous current time are minimized during electrodeposition to deposit the platinum.

Figure 3:
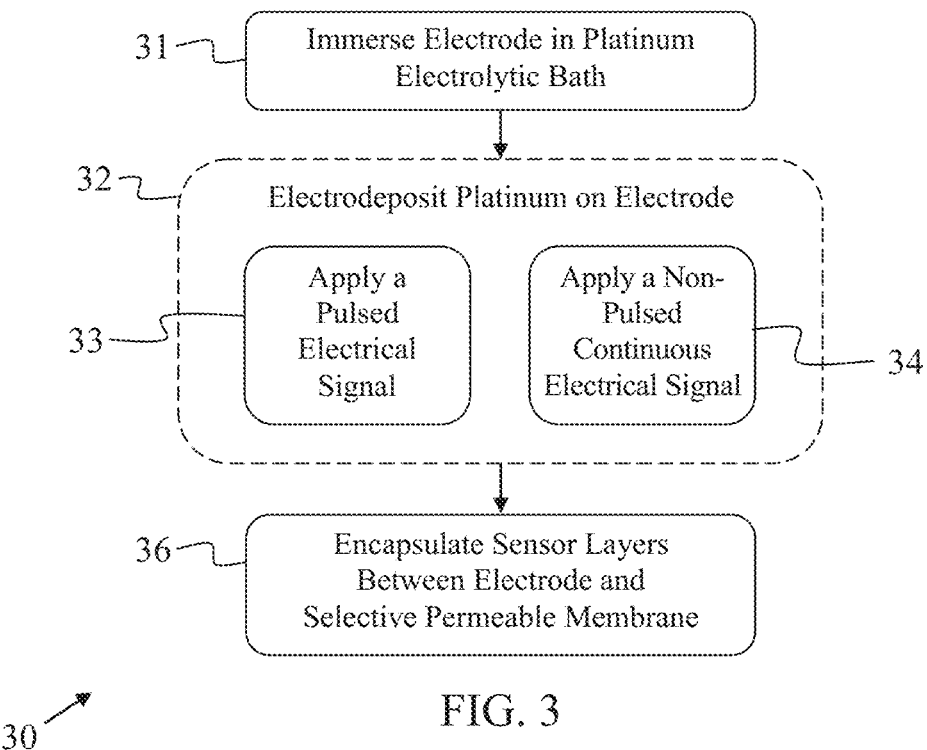
FIGS. 3-6 are flow diagrams illustrating methods for forming exemplary physiological characteristic sensors in accordance with various embodiments.

Referring to FIG. 3, the method 30 for forming the physiological characteristic sensor is illustrated. The method includes application of an electrodeposition process using a hybrid pulse/continuous signal. In an electrodeposition process, particles of a metal or metals are reduced from metal precursors (usually chlorides) contained in an electrolyte with acids such as sulfuric acid, nitric acid, perchloric acid, or hydrochloric acid. An electrical signal, usually with a negative polarity, is applied on a conductive substrate, so that the substrate becomes negatively charged (as a cathode), and a counter electrode (usually a non-polarized electrode such as a platinum electrode) becomes positively charged (as anode). Metallic ions in the solution exchange electrons with the negative substrate and are then deposited onto the substrate.

The hybrid pulse/continuous electrodeposition process described herein applies, separately and sequentially, a pulsed electrical signal and a non-pulsed continuous electrical signal to the sensor electrode to electrodeposit platinum thereon. To do so, the method includes immersing the sensor electrode or electrodes 11 in a platinum electrolytic bath at step 31. An exemplary platinum electrolytic bath is a solution of hydrogen hexachloroplatinate ($H_2PtCl_6$) and lead acetate trihydrate ($Pb(CH_3COO)_2 \cdot 3H_2O$), although other suitable electrolytic baths may be used.

The hybrid pulse/continuous electrodeposition process is performed at step 32 to electrodeposit platinum on the sensor electrode. As shown, the hybrid pulse/continuous electrodeposition process includes applying a pulsed electrical signal at step 33 and applying a non-pulsed continuous electrical signal at step 34. Steps 33 and 34 may be performed in either order. In an exemplary process, steps 33 and 34 may be performed immediately one after the other, or with a break of from about two seconds to about five seconds between steps 33 and 34. It is possible that there may be a longer break, such as for minutes or hours, between steps 33 and 34. While examples of pulsed and continuous electrical signals are provided herein as having pulsed currents and continuous currents, the pulsed and continuous electrical signals may instead or additionally include signals with pulsed voltages and signals with continuous voltages.

Three variables that are characteristic of a "pulsed" current are the duty cycle, peak current density, and number of repeated cycles. Duty cycle is calculated as a ratio between the ON-time (T_On) and combined ON- and OFF-time according to the equation:

$$\text{Duty Cycle} = T\_On/(T\_on+T\_off)$$

Duty cycle is a major factor in distinguishing between a pulsed and continuous current. Based on the journal article, "Pulse and pulse reverse plating—Conceptual, advantages and applications (2008)," pulse plating usually involves a duty cycle of 5% or greater in practice.

With continuous or direct current, there is no second current. Therefore, T_off is 0 and the duty cycle is 100%. Further, there is no repetition (i.e. repeated cycles) for a continuous or direct current. Thus, as used herein, the "pulsed" current is a cycle of a first current followed by second current (or a 0 µA current) wherein the second current is different than the first current and wherein the cycle is repeated. As used herein, a "continuous" current uses a single current for a given period of time with no second current and does not exceed 1 cycle.

After the hybrid pulse/continuous electrodeposition process 32 is completed, the method 30 continues at step 36 with the encapsulation of sensor layers between the electrode and a selective permeable membrane. The selective permeable membrane acts as a glucose limiting membrane during operation as a glucose sensor and limits excess glucose molecules from reacting with immobilized enzyme molecules while maximizing the availability of oxygen.

In an exemplary embodiment, the sensor layers include an analyte sensing layer, such as an enzyme. An exemplary enzyme is glucose oxidase (GOx). Over the enzyme is a protein layer. An exemplary protein layer is human serum albumin (HSA) The HSA may be spray coated over the enzyme layer. An adhesion promoting composition is provided over the protein layer. The adhesion promoting composition assists in adhesion between the selective permeable membrane and the enzyme (GOx)/protein (HSA) matrix.

It is envisioned that the hybrid pulse/continuous electrodeposition process 32 may be performed in a variety of embodiments. In a simplified process, step 33 may be performed first, followed by step 34. For example, a pulsed current may be applied to the sensor electrode by alternating a first current and a second current (or no current). In an exemplary embodiment, the first current and second current are applied for duration of about 0.1 to about 5 seconds, such as for about 2 seconds. The first and second currents may be alternated for a desired number of cycles, such as from about 100 to about 300 cycles. The first current may be from about −50 µA to about −140 µA. The second current may be zero µA to −40 µA. After application of the pulsed current is completed, the continuous direct current may be applied to the sensor electrode for a duration of from about 50 seconds to about 210 seconds. An exemplary continuous direct current is from about −50 µA to about −110 µA.

In other embodiments, the hybrid pulse/continuous electrodeposition process 32 includes performing step 34 first, followed by step 33. For example, a continuous direct current of from about −70 µA to about −110 µA may be applied to the sensor electrode. The continuous direct current may be applied for a duration of from about 120 seconds to about 300 seconds, such as from about 180 seconds to about 240 seconds, for example for about 210 seconds. Then, a pulsed current may be applied to the sensor electrode. For example, a first current and a second current (or no current) may be alternated. An exemplary pulsed current is in the form of an alternating square pulse waveform. In an exemplary embodiment, the first current and second current are applied for duration of about 0.1 to about 5 seconds, such as for about 2 seconds. The first and second currents may be alternated for a desired number of cycles, such as from about 100 to about 200 cycles. The first current may be from about −90 µA to about −110 µA, such as about −103 µA. The second current may be zero µA, i.e., no current.

Figure 4:
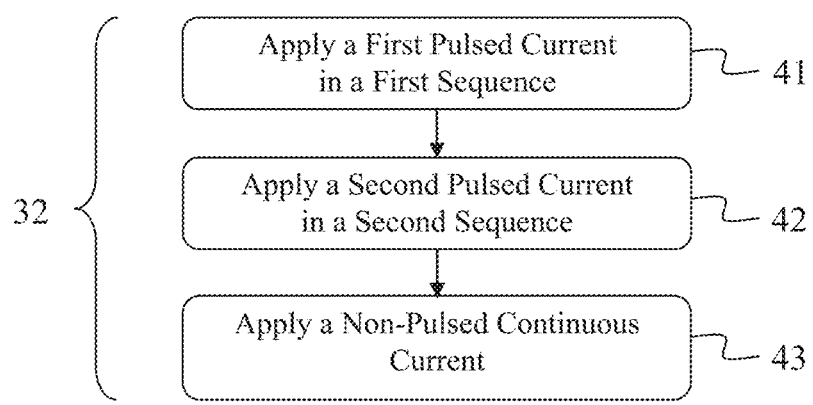

Referring to FIG. 4, the hybrid pulse/continuous electrodeposition process 32 may include more than one process for either or each step 33 and 34. Specifically, in FIG. 4, a first pulsed current is applied to the sensor electrode in step 41 and a second pulsed current is applied to the sensor electrode in step 42. The amperage of either or both alternated currents, pulse duration, or number of cycles may be the same for steps 41 and 42. In an exemplary embodiment, the first sequence at step 41 includes a relatively higher first current, such as from about −90 µA to about −120 µA, and a lower second current, such as about zero µA. Further, the exemplary second sequence at step 42 includes a relatively higher first current, such as from about −80 µA to about −92 µA, and a relatively lower second current, such as from about −80 µA to about −85 µA. In other words, the first sequence has a broader range in amperage between alternating currents than the second sequence. Further, the first sequence may include a relatively higher number of cycles, such as about 120 to 200 cycles, while the second sequence may include a relatively lower number of cycles, such as from about 10 to about 30 cycles. The first currents and second currents may be applied for duration of about 0.1 to about 5 seconds, such as for about 2 seconds in each sequence.

After completion of steps 41 and 42, the hybrid pulse/continuous electrodeposition process 32 may include a single application of a continuous direct current of from about −70 µA to about −110 µA to the sensor electrode. An exemplary continuous direct current is applied for a duration of from about 60 seconds to about 200 seconds.

Figure 5:
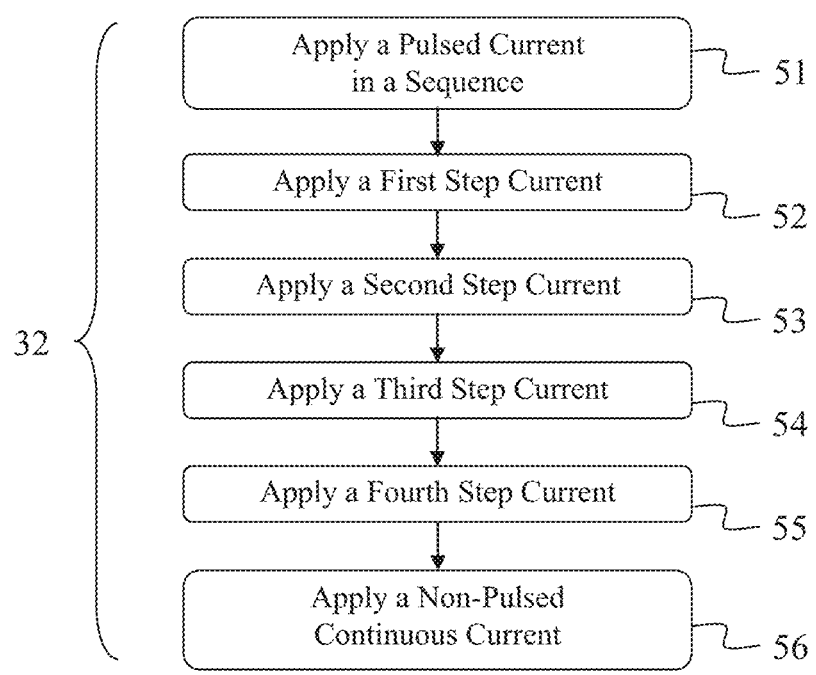

In FIG. 5, another embodiment of the hybrid pulse/continuous electrodeposition process 32 is illustrated. The embodiment of FIG. 5 utilizes a first pulsed current at step 51. Then, four step currents are applied in sequence in steps 52, 53, 54, and 55. It is noted that fewer or more step currents may be applied. Typically, the step currents are applied for short durations, such as less than 5 seconds, for example for about 1 second. Further, the step currents may increase in magnitude and duration in the sequence. After application of the step currents is completed, a non-pulsed continuous current is applied at step 56. The order of steps may be rearranged such that the non-pulsed continuous current is applied before the step currents and the pulsed current applied after the step currents.

Figure 6:
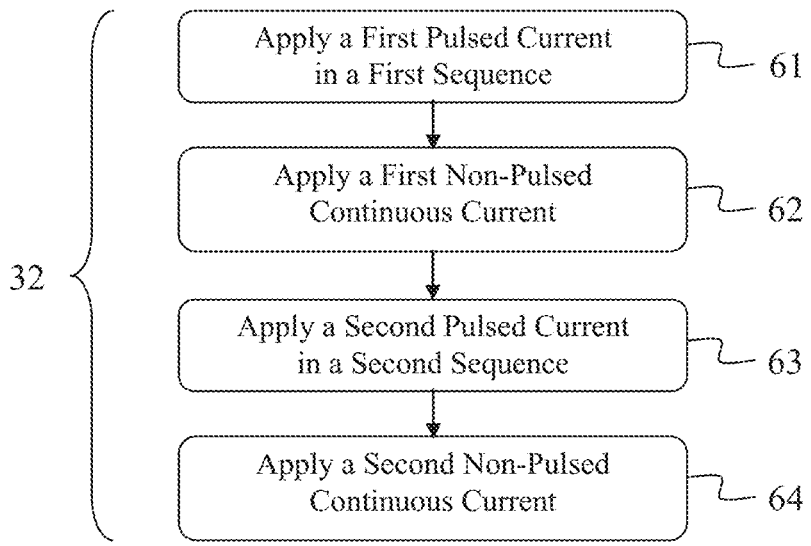

FIG. 6 illustrates another embodiment of the hybrid pulse/continuous electrodeposition process 32. As shown, pulsed currents and continuous currents may be alternated as steps 61, 62, 63, and 64. Steps 61 and 63 may be the same or similar. Likewise, steps 62 and 64 may be the same or similar. Further, the order of steps may be rearranged such that the non-pulsed continuous currents are applied before the respective pulsed currents.

Figure 7:
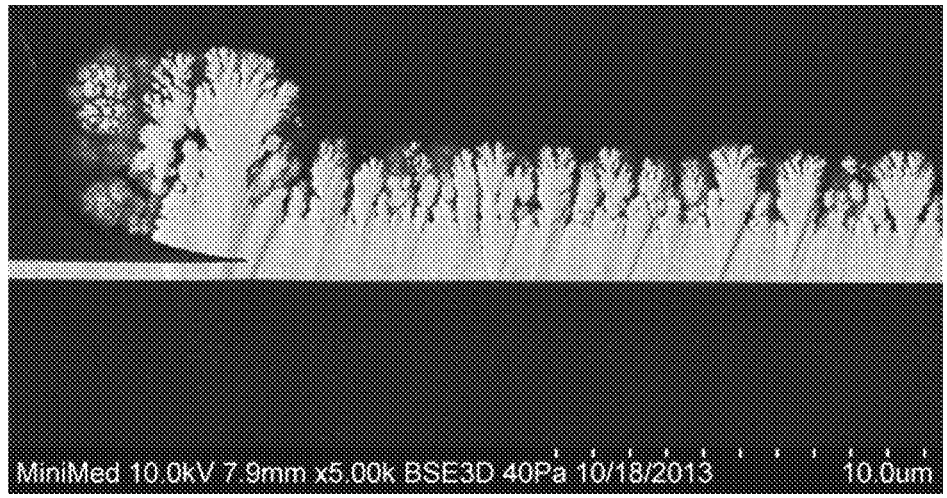
FIG. 7 is a scanning electron microscope/focused ion beam photograph of a platinum deposit obtained from a hybrid pulse/continuous electrodeposition process in accordance with the embodiment of FIG. 6.

FIG. 7 is a scanning electron microscope/focused ion beam photograph of a portion of a platinum deposit forming a counter electrode and obtained from a hybrid pulse/continuous electrodeposition process in accordance with the steps of FIG. 6. As shown, the upper surface of the platinum deposit includes valleys or chasms having depths substantially equal to half the thickness of the platinum deposit.

Figure 8:
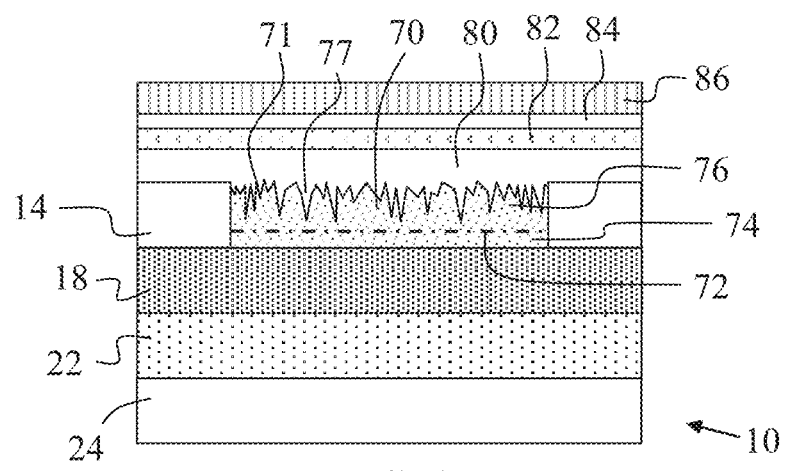
FIG. 8 is a cross-sectional view of a single micro-circle in an electrode subsection in an exemplary embodiment of a physiological characteristic sensor after formation processing.

In FIG. 8, further processing of the sensor 10 is performed after platinum deposition. As shown, the platinum deposit 70 is formed on the exposed portion of the metallization layer 18. The platinum deposit 70 has a rough upper surface 71 such that the electrochemical real surface area is at least about 80 times greater than the cross-sectional area along cross section 72 (the cross sectional area is substantially equal to the area of the exposed metallization layer 18). An exemplary electrochemical real surface area is at least about 100 times greater, or at least about 200 times greater, for example at least about 300 times greater, such as about 370 times greater, than the cross-sectional area along cross section 72. In certain embodiments, the electrochemical real surface area is from about 200 to about 400 times greater than the cross-sectional area along cross section 72.

The platinum deposit 70 is formed with a continuous base portion 74. In an exemplary embodiment, the platinum is dense and uniform in the base portion 74. Further, the platinum deposit 70 is formed with a discontinuous upper portion 76 that forms the upper surface 71. As shown, the discontinuous upper portion 76 is interrupted by valleys or chasms 77 formed in the upper surface 71. In an exemplary embodiment, the thickness or height of the base portion 74 is from about 0.6 to about 1.2 µm, such as about 1.0 µm, and the thickness or height of the upper portion 76 is from about 0.6 to about 2.4 µm. It is believed that the initial pulse electrodeposition sequence helps develop a compact base layer of platinum while the continuous (direct current) sequence creates a rough layer on top of the compact base layer. By introducing more cycles into the pulse deposition process, the thickness of the compact layer will become greater. The continuous component (direct current) influences the roughness of the platinum deposit. Longer continuous current times will contribute to a thicker rough layer. When using a larger current (and consequently larger current density) and longer deposition times during continuous current electroplating, the thickness of rough platinum deposition tends to be much more pronounced at the edges of the electrode.

FIG. 8 further illustrates the formation of sensor layers between the platinum deposit 70 and a selective permeable membrane in accordance with step 36 of FIG. 3. As shown, an analyte sensing layer 80, including a catalyst or reagent, is formed over the platinum deposit 70 (and the patterned insulation layer 14 surrounding the platinum deposit 70. An exemplary analyte sensing layer 80 includes an enzyme. An exemplary enzyme is glucose oxidase (GOx). In the illustrated embodiment, a protein layer 82 is formed over the analyte sensing layer 80. An exemplary protein layer 82 is human serum albumin (HSA). The HSA may be spray coated over the enzyme layer 80. As shown, an adhesion promoting layer 84 is provided over the protein layer. The adhesion promoting layer 84 assists in adhesion between the enzyme (GOx)/protein (HSA) layers and the selective permeable membrane 86. An exemplary selective permeable membrane 86 is a polyurethane/polyuria block copolymer composed of hexamethylene diisocyanate, aminopropyl-terminated siloxane polymer and polyethylene glycol.

While various embodiments of the hybrid pulse/continuous electrodeposition process 32 have been illustrated, they are provided without limitation and other embodiments are contemplated. As described, the hybrid pulse/continuous electrodeposition process 32 includes application of at least one non-pulsed continuous current to the sensor electrode and application of at least one pulsed current to the sensor electrode. Examples of the hybrid pulse/continuous electrodeposition process are provided without limitation.

Example 1

A sensor with two working electrodes in a distributed pattern of micro-circles having a 40 µm diameter was electroplated in a solution of hydrogen hexachloroplatinate $(H_2PtCl_6)$ and lead acetate trihydrate $(Pb(CH_3COO)_2 \cdot 3H_2O)$ from application of a continuous direct current of −103 µA for 210 seconds, followed by application of a pulsing sequence with an initial biased current of −103 µA for two seconds, followed by zero µA current (no current) for 2 seconds, repeated for 165 cycles.

Example 2

A sensor with two working electrodes in a distributed pattern of micro-circles having a 40 µm diameter was electroplated in a solution of hydrogen hexachloroplatinate $(H_2PtCl_6)$ and lead acetate trihydrate $(Pb(CH_3COO)_2 \cdot 3H_2O)$ from application of a continuous direct current of −85 µA for 210 seconds, followed by application of a pulsing sequence with an initial biased current of −103 µA for two seconds, followed by zero µA current (no current) for 2 seconds, repeated for 185 cycles.

Example 3

A sensor with two working electrodes in a distributed pattern of micro-circles having a 40 µm diameter was electroplated in a solution of hydrogen hexachloroplatinate $(H_2PtCl_6)$ and lead acetate trihydrate $(Pb(CH_3COO)_2 \cdot 3H_2O)$ from application of a pulse current with an initial biased current of −103 µA for two seconds, followed by zero µA current (no current) for 2 seconds, repeated for 185 cycles, followed by a continuous direct current of −85 µA for 210 seconds.

Example 4

A sensor with two working electrodes in a distributed pattern of micro-circles having a 40 µm diameter was electroplated in a solution of hydrogen hexachloroplatinate $(H_2PtCl_6)$ and lead acetate trihydrate $(Pb(CH_3COO)_2 \cdot 3H_2O)$ from application of a pulse current with an initial biased current of −103 µA for two seconds, followed by zero µA current (no current) for 2 seconds, repeated for 185 cycles, followed by another sequence of a pulse current with an initial biased current of −89 µA for two seconds, followed by −81 µA current for 2 seconds, repeated for 17 cycles, followed by application of a continuous direct current of −85 µA for 145 seconds.

Example 5

A sensor with two working electrodes in a distributed pattern of micro-circles having a 40 µm diameter was electroplated in a solution of hydrogen hexachloroplatinate $(H_2PtCl_6)$ and lead acetate trihydrate $(Pb(CH_3COO)_2 \cdot 3H_2O)$ from application of a pulse current with an initial biased current of −103 µA for two seconds, followed by zero µA current (no current) for 2 seconds, repeated for 145 cycles, followed by another sequence of a pulse current with an initial biased current of −89 µA for two seconds, followed by −81 µA current for 2 seconds, repeated for 25 cycles, followed by application of a continuous direct current of −85 µA for 210 seconds.

Example 6

A sensor with two working electrodes in a distributed pattern of micro-circles having a 48 µm diameter was electroplated in a solution of hydrogen hexachloroplatinate ($H_2PtCl_6$) and lead acetate trihydrate ($Pb(CH_3COO)_2 \cdot 3H_2O$) from application of a pulse current with an initial biased current of −120 μA for two seconds, followed by zero μA current (no current) for 2 seconds, repeated for 125 cycles, followed by a continuous direct current of −98 μA for 125 seconds.

SAR measurements pertaining to Example 6 (two working electrode sensor) are provided in Tables A-E below in relation to examples of conventional continuous current (direct current) electrodeposition. Specifically, Tables A-D provide SAR data for platinum deposits formed by prior art continuous current electrodeposition, while Table E provides SAR data for platinum deposits formed according to Example 6. For conventional continuous current (direct current) electrodeposition, the surface area ratio of platinum deposition may increase by increasing the current density. However, the electrodeposited platinum may extend beyond the area of the insulation wall when increasing the current density as evidenced in the SEM images of a working electrode formed with a continuous current of −98 μA applied for 210 seconds in FIGS. 9-10 and a working electrode formed with a continuous current of −120 μA applied for 210 seconds in FIGS. 11-12. When using the hybrid pulse/continuous deposition method, the surface area ratio may be increased to from about 350 and to about 400 while the platinum deposit remains confined within the interior of the insulation as shown in the SEM images of FIGS. 13-14 for a working electrode formed with a pulse current with an initial biased current of −120 μA for two seconds, followed by −20 μA current for 2 seconds, repeated for 107 cycles, followed by a continuous direct current of −98 μA for 125 seconds according to Example 7. It is noted that the aggregate of all electrodeposited micro-circles in each image of FIGS. 9-10, 11-12, and 13-14 includes one subsection of a working electrode consisting of 3 subsections of aggregate micro-circles. An additional 3 subsections of aggregate micro-circles make up a second working electrode).

TABLE A

Conventional DC Plating (Prior Art)
Continuous current of −98 μA for 210 seconds

| | Surface Area (uC) | RSA (cm$^2$) | Surface Area Ratio (SAR) |
|---|---|---|---|
| 4-pin_RD3853-11_15-1WE | 115.945069 | 0.557428216 | 218.4737267 |
| 4-pin_RD3853-11_15-2WE | 120.723345 | 0.580400697 | 227.4773676 |
| 4-pin_RD3853-11_16-1WE | 123.311489 | 0.592843697 | 232.3541723 |
| 4-pin_RD3853-11_16-2WE | 121.68937 | 0.585045048 | 229.2976354 |
| 4-pin_RD3853-11_18-1WE | 130.3 | 0.626442308 | 245.5225292 |
| 4-pin_RD3853-11_18-2WE | 128.337553 | 0.617007466 | 241.8247168 |
| 4-pin_RD3853-11_19-1WE | 118.397355 | 0.569218053 | 223.094536 |
| 4-pin_RD3853-11_19-2WE | 123.686712 | 0.594647654 | 233.0611999 |
| 4-pin_RD3853-11_21-1WE | 116.928014 | 0.562153913 | 220.3258766 |
| 4-pin_RD3853-11_21-2WE | 122.471463 | 0.588805111 | 230.7713227 |
| 4-pin_RD3853-11_23-1WE | 124.392417 | 0.598040466 | 234.3909503 |
| 4-pin_RD3853-11_23-2WE | 122.796085 | 0.590365793 | 231.3830035 |
| 4-pin_RD3853-11_24-1WE | 120.298149 | 0.578356486 | 226.6761765 |
| 4-pin_RD3853-11_24-2WE | 123.914213 | 0.595741409 | 233.489877 |

TABLE B

Conventional DC Plating (Prior Art)
Continuous current of −120 μA for 210 seconds

| | Surface Area (uC) | RSA (cm$^2$) | Surface Area Ratio (SAR) |
|---|---|---|---|
| 4-pin_RD3853-12_1-1WE | 176.189625 | 0.847065505 | 331.9917294 |
| 4-pin_RD3853-12_1-2WE | 176.499763 | 0.848556553 | 332.5761182 |
| 4-pin_RD3853-12_11-1WE | 176.626084 | 0.849163865 | 332.8141432 |
| 4-pin_RD3853-12_11-2WE | 161.351506 | 0.775728394 | 304.0324623 |
| 4-pin_RD3853-12_12-1WE | 177.775567 | 0.854690226 | 334.9800985 |
| 4-pin_RD3853-12_12-2WE | 167.831905 | 0.806884159 | 316.2433905 |
| 4-pin_RD3853-12_2-1WE | 177.691837 | 0.854287678 | 334.8223272 |
| 4-pin_RD3853-12_2-2WE | 176.368662 | 0.84792626 | 332.3290864 |
| 4-pin_RD3853-12_6-1WE | 179.858615 | 0.86470488 | 338.9051577 |
| 4-pin_RD3853-12_6-2WE | 179.112521 | 0.861117889 | 337.4993028 |
| 4-pin_RD3853-12_7-1WE | 178.776965 | 0.859504639 | 336.8670192 |
| 4-pin_RD3853-12_7-2WE | 177.763853 | 0.854633909 | 334.9580259 |
| 4-pin_RD3853-12_9-1WE | 177.954262 | 0.855549337 | 335.316811 |
| 4-pin_RD3853-12_9-2WE | 177.974897 | 0.855648543 | 335.3556933 |

TABLE C

Conventional DC Plating (Prior Art)
Continuous current of −98 μA for 210 seconds

| | Surface Area (uC) | RSA (cm$^2$) | Surface Area Ratio (SAR) |
|---|---|---|---|
| 4-pin_RD3853-3_13-1WE | 110.631174 | 0.531880644 | 208.4608261 |
| 4-pin_RD3853-3_13-2WE | 120.719936 | 0.580384308 | 227.470944 |
| 4-pin_RD3853-3_14-1WE | 120.638314 | 0.579991894 | 227.3171448 |
| 4-pin_RD3853-3_14-2WE | 121.872865 | 0.585927236 | 229.6433926 |
| 4-pin_RD3853-3_15-1WE | 117.297926 | 0.563932337 | 221.0228968 |
| 4-pin_RD3853-3_15-2WE | 125.661972 | 0.604144096 | 236.7831557 |
| 4-pin_RD3853-3_16-1WE | 124.7 | 0.599519231 | 234.9705248 |
| 4-pin_RD3853-3_16-2WE | 121.19471 | 0.582666875 | 228.3655543 |
| 4-pin_RD3853-3_20-1WE | 129.1 | 0.620673077 | 243.2613854 |
| 4-pin_RD3853-3_20-2WE | 120.363315 | 0.578669784 | 226.7989679 |
| 4-pin_RD3853-3_21-1WE | 124.2 | 0.597115385 | 234.0283816 |
| 4-pin_RD3853-3_21-2WE | 120.06946 | 0.577257019 | 226.2452609 |
| 4-pin_RD3853-3_22-1WE | 121.9 | 0.586057692 | 229.6945227 |
| 4-pin_RD3853-3_22-2WE | 121.023467 | 0.581843591 | 228.0428834 |

TABLE D

Conventional DC Plating (Prior Art)
Continuous current of −120 μA for 210 seconds

| | Surface Area (uC) | RSA (cm$^2$) | Surface Area Ratio (SAR) |
|---|---|---|---|
| 4-pin_RD3894-4_15-1WE | 170.807054 | 0.82118776 | 321.8494236 |
| 4-pin_RD3894-4_15-2WE | 168.688512 | 0.811002462 | 317.8574835 |
| 4-pin_RD3894-4_16-1WE | 171.258079 | 0.823356149 | 322.6992839 |
| 4-pin_RD3894-4_16-2WE | 169.833587 | 0.81650763 | 320.0151329 |
| 4-pin_RD3894-4_18-1WE | 175.285645 | 0.842719447 | 330.2883721 |
| 4-pin_RD3894-4_18-2WE | 174.344817 | 0.838196236 | 328.5155826 |
| 4-pin_RD3894-4_19-1WE | 171.868423 | 0.826290495 | 323.8493469 |
| 4-pin_RD3894-4_19-2WE | 172.33055 | 0.82851226 | 324.7201265 |
| 4-pin_RD3894-4_21-1WE | 171.924279 | 0.826559034 | 323.9545956 |
| 4-pin_RD3894-4_21-2WE | 172.803187 | 0.830784553 | 325.61071 |
| 4-pin_RD3894-4_22-1WE | 171.206104 | 0.823106269 | 322.6013481 |
| 4-pin_RD3894-4_22-2WE | 170.2 | 0.818269231 | 320.70556 |
| 4-pin_RD3894-4_23-1WE | 171.799214 | 0.82595776 | 323.7189373 |
| 4-pin_RD3894-4_23-2WE | 172.654801 | 0.830071159 | 325.3311083 |

TABLE E

Hybrid Pulse and Continuous Current Plating
Pulse current of 125 cycles of −120 µA for 2 seconds and 0 µA for
2 seconds, followed by continuous current of −98 µA for 125 seconds

|  | Surface Area (uC) | RSA (cm²) | Surface Area Ratio (SAR) |
|---|---|---|---|
| RD3900-3_1_02WE | 193.64831 | 0.93100149 | 364.8888936 |
| RD3900-3_1_04WE | 195.415343 | 0.939496841 | 368.21849 |
| RD3900-3_1_05WE | 200.327614 | 0.963113529 | 377.4746159 |
| RD3900-3_1_07WE | 200.750928 | 0.965148692 | 378.2722607 |
| RD3900-3_1_11WE | 201.660563 | 0.969521938 | 379.9862737 |
| RD3900-3_1_12WE | 199.813183 | 0.960640303 | 376.5052805 |
| RD3900-3_2_02WE | 196.291106 | 0.94370724 | 369.8686784 |
| RD3900-3_2_04WE | 201.558068 | 0.969029173 | 379.7931437 |
| RD3900-3_2_05WE | 203.200788 | 0.976926865 | 382.8884988 |
| RD3900-3_2_07WE | 202.377217 | 0.972967389 | 381.3366551 |
| RD3900-3_2_11WE | 202.773057 | 0.974870466 | 382.0825311 |
| RD3900-3_2_12WE | 200.940459 | 0.966059899 | 378.6293914 |

Example 7

A sensor with two working electrodes in a distributed pattern of micro-circles having a 48 µm diameter was electroplated in a solution of hydrogen hexachloroplatinate ($H_2PtCl_6$) and lead acetate trihydrate ($Pb(CH_3COO)_2 \cdot 3H_2O$) from application of a pulse current with an initial biased current of −120 µA for two seconds, followed by −20 µA current for 2 seconds, repeated for 107 cycles, followed by a continuous direct current of −98 µA for 125 seconds.

Example 8

A sensor with four working electrodes in a distributed pattern of rectangles was electroplated in a solution of hydrogen hexachloroplatinate ($H_2PtCl_6$) and lead acetate trihydrate ($Pb(CH_3COO)_2 \cdot 3H_2O$) from application of a pulse current with an initial biased current of −104 µA for two seconds, followed by zero µA current (no current) for 2 seconds, repeated for 135 cycles, followed by a continuous direct current of −88 µA for 140 seconds.

Example 9

A sensor with four working electrodes in a distributed pattern of rectangles was electroplated in a solution of hydrogen hexachloroplatinate ($H_2PtCl_6$) and lead acetate trihydrate ($Pb(CH_3COO)_2 \cdot 3H_2O$) from application of a pulse current with an initial biased current of −104 µA for two seconds, followed by zero µA current (no current) for 2 seconds, repeated for 135 cycles, followed by another sequence of a pulse current with an initial biased current of −92 µA for two seconds, followed by −84 µA current for 2 seconds, repeated for 17 cycles, followed by application of a continuous direct current of −88 µA for 72 seconds.

Example 10

A sensor with four working electrodes in a distributed pattern of rectangles was electroplated in a solution of hydrogen hexachloroplatinate ($H_2PtCl_6$) and lead acetate trihydrate ($Pb(CH_3COO)_2 \cdot 3H_2O$) from application of a pulse current with an initial biased current of −67 µA for two seconds, followed by zero µA current (no current) for 2 seconds, repeated for 261 cycles, followed by a continuous direct current of −67 µA for 69 seconds.

Example 11

A sensor with four working electrodes in a distributed pattern of rectangles was electroplated in a solution of hydrogen hexachloroplatinate ($H_2PtCl_6$) and lead acetate trihydrate ($Pb(CH_3COO)_2 \cdot 3H_2O$) from application of a pulse current with an initial biased current of −67 µA for two seconds, followed by zero µA current (no current) for 2 seconds, repeated for 241 cycles, followed by a continuous direct current of −67 µA for 109 seconds.

Example 12

A sensor with four working electrodes in a distributed pattern of rectangles was electroplated in a solution of hydrogen hexachloroplatinate ($H_2PtCl_6$) and lead acetate trihydrate ($Pb(CH_3COO)_2 \cdot 3H_2O$) from application of a pulse current with an initial biased current of −67 µA for two seconds, followed by zero µA current (no current) for 2 seconds, repeated for 221 cycles, followed by a continuous direct current of −67 µA for 149 seconds.

Example 13

Figure 15:
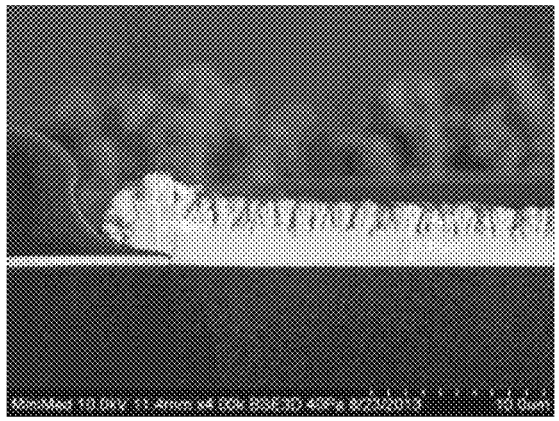
FIGS. 15-18 are ion mill images of a platinum deposit obtained from a hybrid pulse/continuous electrodeposition process in accordance with the embodiments herein.
Figure 16:
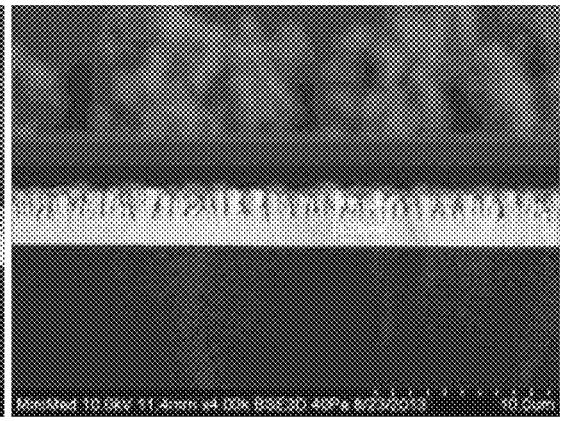

A sensor with working electrodes in a distributed electrode layout was electroplated in a solution of hydrogen hexachloroplatinate ($H_2PtCl_6$) and lead acetate trihydrate ($Pb(CH_3COO)_2 \cdot 3H_2O$) from application of a pulse current with an initial biased current of −67 µA for two seconds, followed by zero µA current (no current) for 2 seconds, repeated for 181 cycles, followed by a continuous direct current of −67 µA for 229 seconds. The electrodeposition forms a base platinum layer with edge portions having a thickness (or height) of about 2.58 µm and a central portion having a thickness of about 1.22 µm to about 1.51 µm and forms an upper platinum region with edge portions having a thickness of about 1.79 µm and a central portion having a thickness of from about 1.61 µm to about 1.74 µm. FIGS. 15 and 16 are ion mill images of an edge portion and a central portion of a platinum deposit formed according to Example 13.

Example 14

Figure 17:
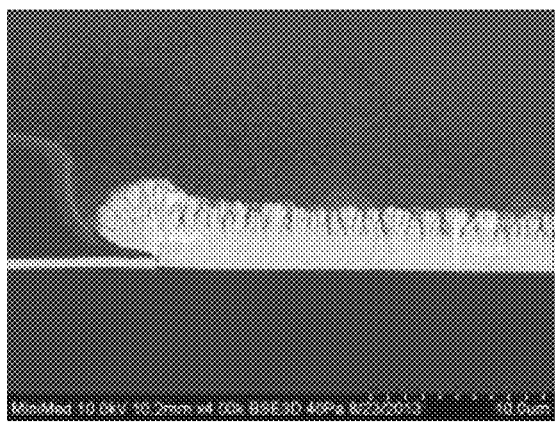
Figure 18:
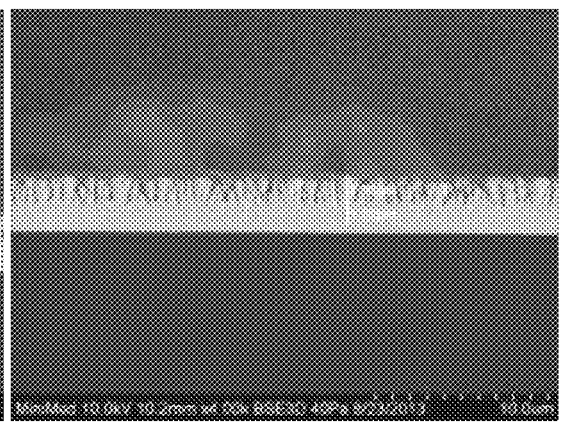

A sensor with working electrodes in a distributed electrode layout was electroplated in a solution of hydrogen hexachloroplatinate ($H_2PtCl_6$) and lead acetate trihydrate ($Pb(CH_3COO)_2 \cdot 3H_2O$) from application of a pulse current sequence with an initial biased current of −67 µA for two seconds, followed by zero µA current (no current) for 2 seconds, repeated for 181 cycles, followed by application of a first step current of −13 µA for one second, a second step current of −26 µA for one second, a third step current of −39 µA for one second, and a fourth step current of −52 µA for one second, not repeated, followed by a continuous direct current of −67 µA for 229 seconds. The electrodeposition forms a base platinum layer with edge portions having a thickness (or height) of about 2.43 µm and a central portion having a thickness of about 1.22 µm to about 1.41 µm and forms an upper platinum region with edge portions having a thickness of about 1.98 µm and a central portion having a thickness of from about 1.56 µm to about 1.71 µm. FIGS. 17 and 18 are ion mill images of the platinum deposit formed according to Example 14.

Table F provides data regarding the roughness average for platinum deposits formed according to Examples 10-14.

TABLE F

| | Roughness Average (um) | | | | |
|---|---|---|---|---|---|
| Sample # | Example 10 | Example 11 | Example 12 | Example 13 | Example 14 |
| 1 | 0.277 | 0.356 | 0.24 | 0.212 | 0.187 |
| 2 | 0.282 | 0.343 | 0.237 | 0.22 | 0.191 |
| 3 | 0.282 | 0.343 | 0.235 | 0.22 | 0.188 |
| 4 | 0.275 | 0.347 | 0.241 | 0.219 | 0.182 |
| 5 | 0.279 | 0.341 | 0.245 | 0.221 | 0.199 |
| 6 | 0.282 | 0.35 | 0.246 | 0.222 | 0.197 |
| 7 | 0.289 | 0.374 | 0.242 | 0.214 | 0.183 |
| 8 | 0.279 | 0.371 | 0.239 | 0.214 | 0.188 |
| 9 | 0.281 | 0.36 | 0.241 | 0.212 | 0.192 |
| 10 | 0.279 | 0.366 | 0.247 | 0.221 | 0.194 |
| 11 | 0.278 | 0.355 | 0.249 | 0.224 | 0.192 |
| 12 | 0.291 | 0.36 | 0.247 | 0.223 | 0.206 |
| 13 | 0.277 | 0.348 | 0.242 | 0.194 | 0.191 |
| 14 | 0.28 | 0.337 | 0.236 | 0.193 | 0.184 |
| 15 | 0.275 | 0.349 | 0.244 | 0.195 | 0.187 |
| 16 | 0.279 | 0.343 | 0.248 | 0.195 | 0.185 |
| 17 | 0.278 | 0.343 | 0.248 | 0.199 | 0.191 |
| 18 | 0.285 | 0.342 | 0.251 | 0.204 | 0.199 |
| 19 | 0.278 | 0.417 | 0.241 | 0.199 | 0.196 |
| 20 | 0.279 | 0.362 | 0.24 | 0.2 | 0.188 |
| 21 | 0.281 | 0.35 | 0.238 | 0.193 | 0.192 |
| 22 | 0.284 | 0.337 | 0.243 | 0.198 | 0.193 |
| 23 | 0.285 | 0.345 | 0.246 | 0.197 | 0.199 |
| 24 | 0.287 | 0.353 | 0.247 | 0.203 | 0.203 |
| 25 | 0.281 | 0.244 | 0.247 | 0.211 | 0.177 |
| 26 | 0.277 | 0.24 | 0.241 | 0.21 | 0.181 |
| 27 | 0.276 | 0.246 | 0.247 | 0.204 | 0.189 |
| 28 | 0.285 | 0.244 | 0.244 | 0.204 | 0.188 |
| 29 | 0.277 | 0.249 | 0.247 | 0.213 | 0.187 |
| 30 | 0.281 | 0.245 | 0.248 | 0.214 | 0.197 |
| 31 | 0.279 | 0.241 | 0.236 | 0.206 | 0.18 |
| 32 | 0.287 | 0.243 | 0.242 | 0.206 | 0.18 |
| 33 | 0.29 | 0.248 | 0.24 | 0.211 | 0.186 |
| 34 | 0.281 | 0.248 | 0.239 | 0.211 | 0.182 |
| 35 | 0.285 | 0.253 | 0.243 | 0.221 | 0.185 |
| 36 | 0.283 | 0.253 | 0.252 | 0.217 | 0.192 |

Example 15

A sensor with working electrodes in a distributed electrode layout was electroplated in a solution of hydrogen hexachloroplatinate ($H_2PtCl_6$) and lead acetate trihydrate ($Pb(CH_3COO)_2 \cdot 3H_2O$) from application of a pulse current with an initial biased current of −73 µA for two seconds, followed by zero µA current (no current) for 2 seconds, repeated for 130 cycles, followed by a continuous direct current of −54 µA for 165 seconds. The electrodeposition forms a base platinum layer with edge portions having a thickness (or height) of about 0.853 µm and a central portion having a thickness of about 0.754 µm and forms an upper platinum region with edge portions having a thickness of about 0.913 µm and a central portion having a thickness of about 0.794 µm.

Example 16

A sensor with working electrodes in a distributed electrode layout was electroplated in a solution of hydrogen hexachloroplatinate ($H_2PtCl_6$) and lead acetate trihydrate ($Pb(CH_3COO)_2 \cdot 3H_2O$) from application of a pulse current with an initial biased current of −73 µA for two seconds, followed by zero µA current (no current) for 2 seconds, repeated for 130 cycles, followed by a continuous direct current of −66 µA for 165 seconds. The electrodeposition forms a base platinum layer with edge portions having a thickness (or height) of from about 1.55 µm to about 2.02 µm and a central portion having a thickness of from about 0.814 µm to about 0.853 µm and forms an upper platinum region with edge portions having a thickness of from about 0.913 µm to about 1.07 µm and a central portion having a thickness of from about 1.37 µm to about 1.49 µm.

Example 17

A sensor with working electrodes was electroplated in a solution of hydrogen hexachloroplatinate ($H_2PtCl_6$) and lead acetate trihydrate ($Pb(CH_3COO)_2 \cdot 3H_2O$) from application of a pulse current with an initial biased current of −165 µA for two seconds, followed by −60 µA current for 2 seconds, repeated for 80 cycles, followed by a continuous direct current of −165 µA for 75 seconds, followed by application of a pulse current with an initial biased current of −165 µA for two seconds, followed by −60 µA current for 2 seconds, repeated for 80 cycles, and followed by a continuous direct current of −165 µA for 75 seconds. Under conditions of alternating square pulse waveform and a direct current, the platinum is deposited with a compact base layer having a thickness (or height) of from about 0.636 µm to about 1.08 µm and to form rough upper regions including edge portions having a thickness of about 3.80 µm to about 4.27 µm, a central portion having a thickness of about 0.788 µm to about 1.66 µm, and a thicker central portion having a thickness of from about 1.63 µm to about 2.29 µm.

Glucose sensors and methods for forming glucose sensors designed to enhance glucose sensing performance are provided herein. As described, methods for forming glucose sensors include performing an electrodeposition process by sequentially applying a pulsed signal to the electrode and applying a non-pulsed continuous signal to the electrode to form a platinum deposit on the electrode. The signal may include pulsed and continuous applications of current and/or voltage. Exemplary platinum deposits have increased surface area as compared to platinum deposits formed by conventional processes.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:
1. A method for forming a physiological characteristic sensor, the method comprising the steps of:
   immersing a sensor electrode in a platinum electrolytic bath; and
   performing an electrodeposition process by sequentially applying a pulsed signal to the sensor electrode, wherein the pulsed signal includes a repeated cycle of a first current and a second current different from the first current, wherein the first current and the second current have a same polarity, and applying a non-pulsed continuous signal to the sensor electrode, wherein the non-pulsed continuous signal includes a non-repeated application of a third current, to form a platinum deposit on the sensor electrode.

2. The method of claim 1 wherein performing the electrodeposition process comprises applying the pulsed signal to the sensor electrode before applying the non-pulsed continuous signal to the sensor electrode.

3. The method of claim 1 wherein performing the electrodeposition process comprises applying the pulsed signal to the sensor electrode after applying the non-pulsed continuous signal to the sensor electrode.

4. The method of claim 1 wherein applying the pulsed signal to the sensor electrode comprises applying the repeated cycle of the first current of between about −50 μA and about −150 μA and the second current of less than 0 μA and about −20 μA.

5. The method of claim 1 wherein applying the pulsed signal to the sensor electrode comprises applying from about 100 to about 300 cycles of the first current and the second current to the sensor electrode.

6. The method of claim 1 wherein applying the pulsed signal to the sensor electrode comprises applying cycles of about 0.1 seconds to about 4 seconds of the first current and about 0.1 seconds to about 4 seconds of the second current to the sensor electrode.

7. The method of claim 1 wherein applying the pulsed signal to the sensor electrode comprises applying a pulsed current in a square pulse pattern.

8. The method of claim 1, wherein immersing the sensor electrode in a platinum electrolytic bath comprises immersing the sensor electrode in a solution of hydrogen hexachloroplatinate ($H_2PtCl_6$) and lead acetate trihydrate ($Pb(CH_3COO)_2 \cdot 3H_2O$).

9. The method of claim 1 wherein applying the pulsed signal to the sensor electrode comprises applying a first pulsed signal to the sensor electrode in a first sequence and applying a second pulsed signal to the sensor electrode in a second sequence.

10. The method of claim 1 wherein applying the pulsed signal to the sensor electrode comprises applying a first pulsed signal to the sensor electrode in a first sequence and applying a second pulsed signal to the sensor electrode in a second sequence and wherein applying the non-pulsed continuous signal to the sensor electrode comprises applying a first non-pulsed continuous signal to the sensor electrode and applying a second non-pulsed continuous signal to the sensor electrode.

11. The method of claim 1, wherein the electrodeposition process forms the sensor electrode with an electrochemical real surface area at least about 80 times greater than a cross sectional area of the sensor electrode.

12. The method of claim 11, wherein the sensor electrode is formed with a platinum coating having the cross sectional area and the electrochemical real surface area, wherein the platinum coating includes a substantially continuous base portion having a thickness of from about 0.5 to about 1.5 μm and a discontinuous upper portion having thickness of from about 0.6 to about 2.5 μm.

13. A method for forming a platinum deposit having a rough surface, the method comprising the steps of:
contacting a deposition site with a platinum electrolyte; and
performing a hybrid pulse/continuous electrodeposition process by sequentially applying a pulsed signal to the deposition site, wherein the pulsed signal includes a repeated cycle of a first current and a second current different from the first current, wherein the first current and the second current have a same polarity, and applying a non-pulsed continuous signal to the deposition site, wherein the non-pulsed continuous signal includes a non-repeated application of a third current, to form the platinum deposit on the deposition site.

14. The method of claim 13 wherein applying the pulsed signal to the deposition site comprises applying cycles of about 0.1 seconds to about 4 seconds of the first current and about 0.1 seconds to about 4 seconds of the second current to the deposition site, and wherein applying the non-pulsed continuous signal to the deposition site comprises applying the third current to the deposition site for from about 50 seconds to about 240 seconds.

15. The method of claim 13 wherein performing the hybrid pulse/continuous electrodeposition process further comprises applying a second pulsed signal to the deposition site, wherein the second pulsed signal includes a repeated cycle of a fourth current and a fifth current different from the fourth current.

16. The method of claim 13, wherein the hybrid pulse/continuous electrodeposition process forms the platinum deposit with an electrochemical real surface area at least about 80 times greater than a cross sectional area of the platinum deposit.

17. The method of claim 16, wherein the hybrid pulse/continuous electrodeposition process forms the platinum deposit with a substantially continuous base portion having a thickness of from about 0.5 to about 1.5 μm and a discontinuous upper portion having thickness of from about 0.6 to about 2.5 μm.

18. The method of claim 1 wherein the first current and the second current each have a negative polarity.

19. The method of claim 13 wherein the first current and the second current each have a negative polarity.

20. The method of claim 19 wherein applying the pulsed signal to the deposition site comprises applying the repeated cycle of the first current of between about −50 μA and about −150 μA and the second current of less than 0 μA and about −20 μA.

* * * * *